United States Patent
Yates et al.

(10) Patent No.: US 9,101,904 B2
(45) Date of Patent: Aug. 11, 2015

(54) AIR PURIFICATION SYSTEM USING ULTRAVIOLET LIGHT EMITTING DIODES AND PHOTOCATALYST-COATED SUPPORTS

(75) Inventors: Stephen Yates, South Barrington, IL (US); Gregory Allan Land, Chicago, IL (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 149 days.

(21) Appl. No.: 13/481,586

(22) Filed: May 25, 2012

(65) Prior Publication Data
US 2013/0313104 A1 Nov. 28, 2013

(51) Int. Cl.
*A61L 9/20* (2006.01)
*B01J 19/12* (2006.01)
*B01J 12/00* (2006.01)

(52) U.S. Cl.
CPC .............. *B01J 19/123* (2013.01); *B01J 12/007* (2013.01); *A61L 9/205* (2013.01); *B01J 2219/0875* (2013.01); *B01J 2219/0892* (2013.01); *B01J 2219/1242* (2013.01); *B01J 2219/1254* (2013.01); *B01J 2219/1296* (2013.01)

(58) Field of Classification Search
CPC ............ A61L 9/205; A61L 9/20; A61L 2/088
USPC ....................................... 422/4, 24
See application file for complete search history.

(56) References Cited

U.S. PATENT DOCUMENTS

| | | | |
|---|---|---|---|
| 5,702,494 A * | 12/1997 | Tompkins et al. | 55/498 |
| 7,125,526 B2 | 10/2006 | Sheehan | |
| 7,767,158 B2 | 8/2010 | Kawai et al. | |
| 7,820,100 B2 * | 10/2010 | Garfield et al. | 422/1 |
| 2003/0150905 A1 * | 8/2003 | Mazzilli | 232/17 |
| 2011/0033346 A1 * | 2/2011 | Bohlen et al. | 422/186.3 |
| 2011/0064638 A1 | 3/2011 | Molins | |
| 2011/0142725 A1 | 6/2011 | Liu et al. | |

FOREIGN PATENT DOCUMENTS

| | | |
|---|---|---|
| CN | 2662131 | 12/2004 |
| CN | 201815244 | 5/2011 |
| JP | 2006296811 | 11/2006 |
| WO | 2011162059 | 12/2011 |

OTHER PUBLICATIONS

Shie et al., Photodegradation kinetics of formaldehyde using light sources of UVA, UVC and UVLED in the presence of composed silver titanium oxide photocatalyst, Journal of Hazardous Materials, 2008, vol. 155, pp. 164-172, Taiwan.

Mo et al., Photocatalytic purification of volatile organic compounds in indoor air: A literature review, Atmospheric Environment, 2009, pp. 2229-2246, vol. 43.

(Continued)

*Primary Examiner* — Sean E Conley
*Assistant Examiner* — Donald Spamer
(74) *Attorney, Agent, or Firm* — Shimokaji IP

(57) ABSTRACT

An air cleaning system may provide effective and evenly distributed removal of organic contaminants from airflow. An ultraviolet light emitting diode (UV LED) source may emit ultraviolet light onto a photocatalyst on a support in airflow where airflow is between the UV LED source and the photocatalyst.

11 Claims, 5 Drawing Sheets

(56) References Cited

OTHER PUBLICATIONS

Masakazu Anpo, Utilization of TiO2 photocatalysts in green chemistry, Pure Appl. Chem., 2000, vol. 72, No. 7, pp. 1265-1270, Japan.
Kisch et al., Daylight Photocatalysis by Carbon-Modified Titanium Dioxide, Angewandte Chemie, 2003, vol. 42, pp. 4908-4911.
Kisch et al., Visible-Light Photocatalysis by Modified Titania, Chemphyschem, 2002, vol. 3, pp. 399-400.

Diwald et al., Photochemical Activity of Nitrogen-Doped Rutile TiO2(IIO) in Visible Light, Journal of Physical Chemistry, 2004, Vo. 108, pp. 6004-6008.
Yin et al., Preparation of nitrogen-doped titania with high visible light induced photocatalytic activity by mechanochemical reaction of titania and hexamethylenetetramine, Journal of Materials Chemistry, Oct. 17, 2003, vol. 13, 2996-3001.

* cited by examiner

AIR PURIFICATION SYSTEM USING ULTRAVIOLET LIGHT EMITTING DIODES AND PHOTOCATALYST-COATED SUPPORTS

BACKGROUND OF THE INVENTION

The present invention generally relates to air purification systems, and more particularly, to an air purification system using ultraviolet light emitting diodes (LED) and photocatalyst-coated supports.

The use of recirculated air may be common within inhabited enclosures. In some cases, airflow may be necessarily recirculated to provide breathable air where air external to the enclosure may not be viable. In other cases, it may be more economical to use recirculated air which has already been adjusted to the correct temperature and humidity. For example, pressurized cabins in aircraft may commonly recirculate a portion of the air rather than try to circulate only external air into the cabin. One result of using recirculated air is that organic contaminants may increase in concentration and may be passed to the inhabitants of the cabin.

One approach to removing contaminants from airflow is to use a photocatalytic air cleaner on airflow. It may be known to use for example, mercury vapor lamps to irradiate a photocatalyst in contact with airflow. Lamps may produce a heterogeneously distributed intensity across a photocatalyst. This may result in portions of the airflow which are less well treated, and still contain contaminants. Mercury vapor lamps may also be commonly made of glass or quartz, and, therefore not useful in environments where mechanical shock might result in their shattering. In addition, the use of lamps may result in insufficient energy absorption by the photocatalyst to provide effective catalysis. This can occur if the emission spectrum of the lamps does not overlap with the absorption spectrum of the photocatalyst.

In some purification systems, titanium dioxide based photocatalysts may be employed. The absorbance of titanium dioxide for photocatalysis drops rapidly with increasing wavelength, and is negligible above 410 nanometers. At wavelengths at which the photocatalyst does not absorb light, no reaction will occur, so use of a light source whose emittance spectrum overlaps poorly with the absorption spectrum of the photocatalyst can result in poor efficiency. It may be desirable to operate a photocatalytic device using a light source which has a wavelength higher than that normally absorbed by titanium dioxide. In some cases, the absorbance spectrum of titanium dioxide may be shifted to higher wavelengths by, for example, doping titanium dioxide with nitrogen or carbon. The effectiveness of titanium based photocatalysts may be short lived as the doped element may degrade quickly and the titanium dioxide is again ineffective at wavelengths above 410 nm.

As can be seen, there is a need for an air cleaning system that may provide efficient and evenly distributed photocatalysis in airflow.

SUMMARY OF THE INVENTION

In one aspect of the present invention, an air cleaning system comprises an ultraviolet light emitting diode (UV LED); a support disposed proximate to the UV LED; and a photocatalyst on the support disposed to contact airflow passing across or through the support, wherein: airflow is between the UV LED and the photocatalyst and, the UV LED is positioned to emit ultraviolet light onto the photocatalyst.

In another aspect of the present invention, an air cleaning system comprises a chamber; an ultraviolet light emitting diode (UV LED) positioned to emit ultraviolet light into the chamber; a plurality of support plates in the chamber spaced parallel to one another, wherein at least one of the plates is disposed proximate the UV LED; and a photocatalyst on the support plates disposed to contact airflow passing across or between the support plates, wherein the UV LED is positioned to emit ultraviolet light onto the photocatalyst.

In yet another aspect of the present invention, a method of purifying airflow comprises passing the airflow through a reactor including an ultraviolet light reactive photocatalyst; emitting ultraviolet light from an ultraviolet light emitting diode into the airflow and onto the photocatalyst; and removing organic contaminants from the airflow that makes contact with the photocatalyst while the ultraviolet light is emitted on the photocatalyst.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

The present invention generally provides an air cleaning system that removes organic contaminants from airflow. Exemplary embodiments of the present invention may be used, for example, in enclosed quarters where airflow may be recirculated and individuals may be subjected to breathing in air that aggregates organic contaminants.

Figure 1B:
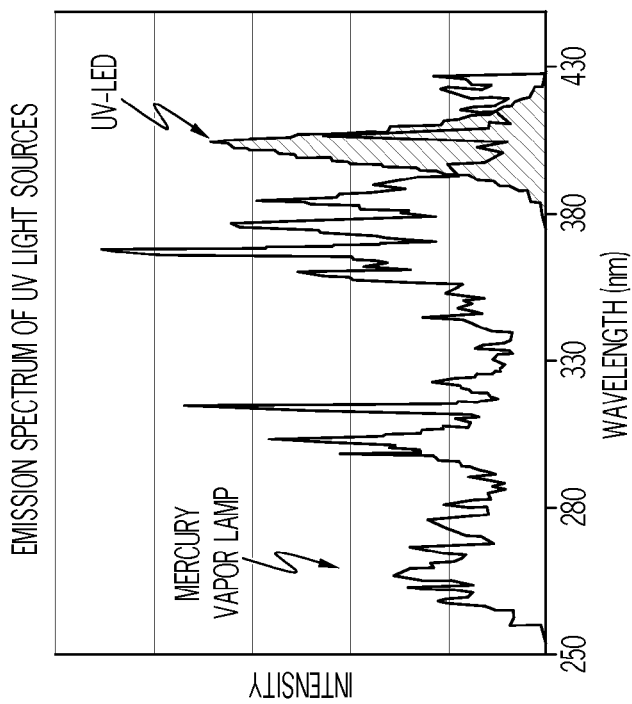
FIG. 1B is a plot showing the emission spectra of a UV LED compared to that for a mercury vapor lamp.
Figure 1A:
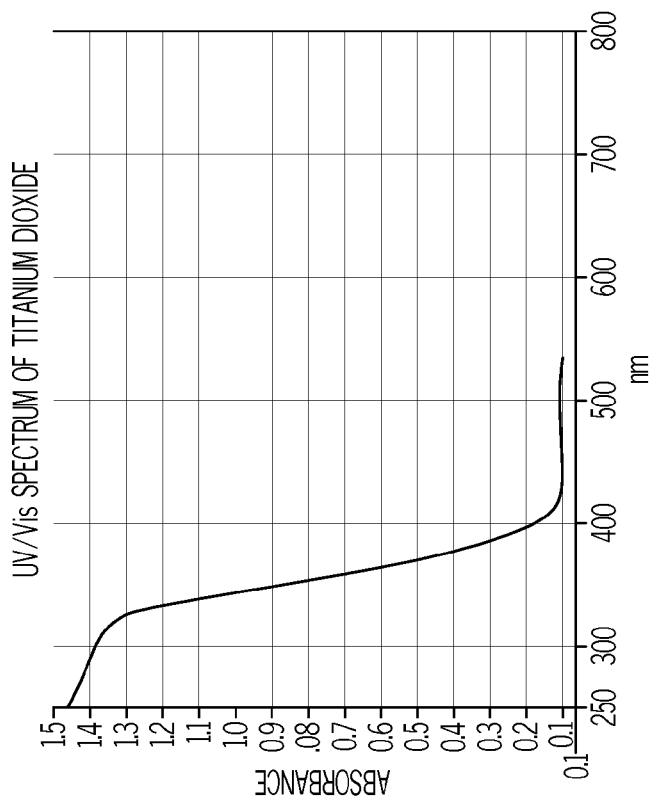
FIG. 1A is a plot showing the absorbance spectrum of titanium dioxide between 250 nm and 800 nm wavelengths.

In one aspect, exemplary embodiments of the present invention may use, for example, titanium dioxide as a photocatalyst irradiated with ultraviolet light (UV). The ultraviolet light source employed may be a light emitting diode (LED) whose emission wavelength is centered approximately near 400 nm. As may be seen in FIG. 1A, the absorbance spectrum of titanium dioxide at about 400 nm may be relatively low (approximately 0.15 absorbance) compared to wavelengths of 350 nm or less; just 50 nm difference (approximately 0.9 absorbance). Referring to FIG. 1B, a comparison between the wavelength distribution for a mercury vapor lamp to an UV LED (shaded) is shown. Mercury vapor lamps (which may be currently used for photocatalysis) may have an emission spectrum which overlaps most of the absorption spectrum of titanium dioxide; approximately 255 nm to 430 nm. The UV LED emission spectrum may overlap only a portion of the absorption spectrum of titanium dioxide; approximately 380 nm to 430 nm. The peak intensity for the emission spectrum of the UV LED is centered at approximately 410 nm, near the lower end of absorption spectrum for titanium dioxide. One ordinarily skilled in the art may conclude from the mismatch between the emission spectrum of the LED and the absorption spectrum of titanium dioxide that a photocatalytic reaction using titanium dioxide may not be effective. As a result, photocatalytic reactions are normally carried out using light sources which provide lower wavelengths, such as a mercury vapor lamp. Nonetheless, exemplary embodiments disclosed herein, using a photocatalytic reactor employing a UV LED with this emission spectrum and titanium dioxide as a photocatalyst may be highly effective.

Figure 2:
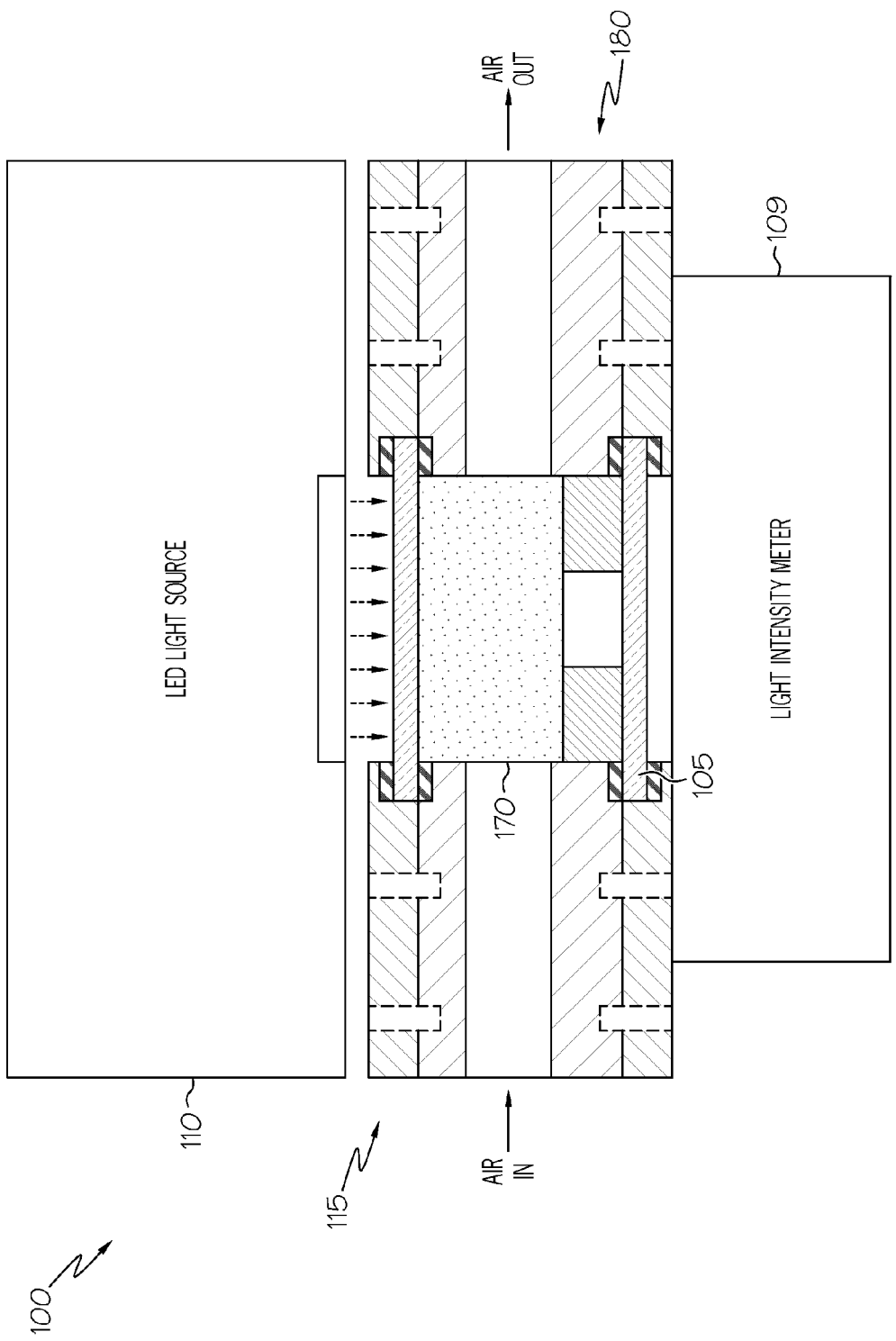
FIG. 2 is a block diagram of an air cleaning system in accordance with an exemplary embodiment of the present invention.

Referring to FIG. 2, an air cleaning system 100 is shown according to an exemplary embodiment of the present invention. FIG. 2 shows the air cleaning system 100 represented as a block diagram showing airflow relative to ultraviolet light emission. The air cleaning system 100 may include an ultraviolet UV light source 110, such as an ultraviolet light emitting diode (UV-LED) and a photocatalyst 170. Quartz windows 105 may be between the UV light source 110 and the photocatalyst 170 and between the photocatalyst 170 and a light meter 109. The light meter 109 may be used in embodiments monitoring the light output from the UV light source 110. A reactor 180 including the photocatalyst 170 may be inside a chamber 115. The photocatalyst 170 may be positioned in the airflow so that organic contaminants (not shown) in the airflow make contact with the photocatalyst 170 in the reactor 180. The UV light source 110 may be positioned to emit ultraviolet light onto the photocatalyst 170 to produce a reaction between the photocatalyst 170 and the organic contaminants (not shown) in the airflow, absorbing the organic contaminants and removing them from airflow.

Figure 3:
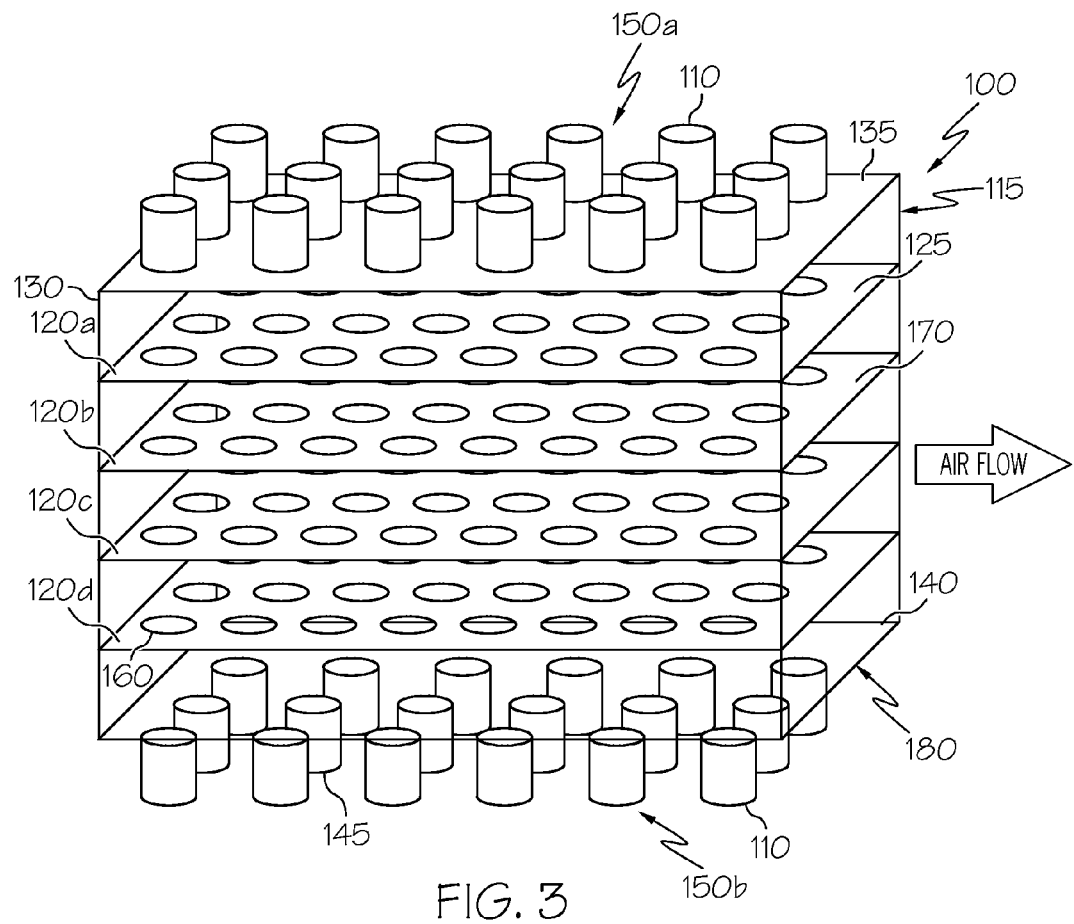
FIG. 3 is a perspective side view of an air cleaning system in accordance with another exemplary embodiment of the present invention.
Figure 3A:
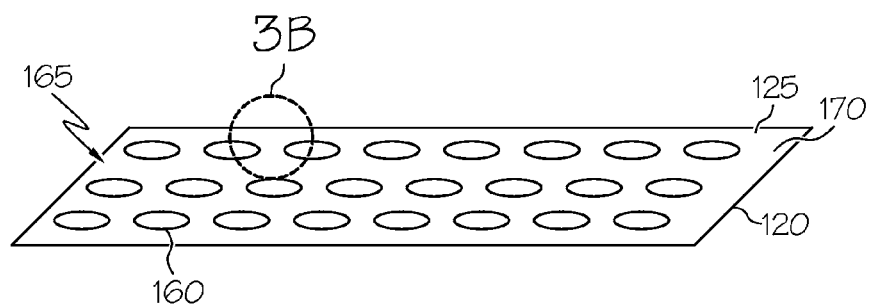
FIG. 3A is a perspective side view of a support plate of the air cleaning system of FIG. 3.

Referring now to FIGS. 3 and 3A, the air cleaning system 100 is shown with greater detail in accordance with an exemplary embodiment of the present invention. The chamber 115 may be disposed within airflow so that the airflow passes through an entrance end 130 and out an egress end 140. The reactor 180 may be positioned between the entrance end 130 and the egress end 140. The reactor 180 may include a support 120 holding the photocatalyst 170. In an exemplary embodiment, the support 120 may be a plate. The support 120 may sometimes be referred to as a plate(s) 120 or as support plate(s) 120 in the following description. The photocatalyst 170 may be placed on a surface 125 of the support 120. For sake of illustration, only one surface 125 is shown, however, it will be understood that the photocatalyst 170 may be attached to both sides (surfaces) of the support 120. The support 120 may be positioned in the chamber 115, orthogonal to airflow so that airflow passes across the surface 125.

In one exemplary embodiment, the reactor 180 may include a plurality of the support plates 120 supported by the chamber 115. The plates 120 (shown as plates 120a, 120b, 120c, and 120d) may be spaced parallel from one another. In one aspect, spacing of the plates 120 and the air velocity there through can be adjusted to ensure adequate contact between the air and the photocatalyst 170. In an exemplary embodiment, the plates 120 may include one or more perforations 160. The perforations 160 may be arranged as a set 165. It may be appreciated that some airflow passing over surface 125 of a support plate 120 may pass through one of the perforations 160 and flow along the underside (not shown) of the plate 120 making contact with photocatalyst 170 on said underside. While the support 120 is shown as a plate, other exemplary embodiments may use supports 120 which are not flat. For example, the support 120 may be corrugated to enhance air mixing.

It may also be appreciated that there may be a tradeoff between the size and number of perforations 160 in plates 120 and the amount of surface area available for photocatalytic reaction. The reactor 180 may be configured to optimize irradiation of the photocatalyst 170 on the outermost plates (120a and 120d) and underlying plates (120b and 120c). In exemplary embodiments where a plurality of support plates 120 are used, the set of perforations 165 of two adjacent support plates 120 may not line up to one another. For example, the set of perforations 165 of plate 120b may not have centers lined up with the centers of the set of perforations 165 of plate 120a. Light entering at any angle should at some depth impinge on a catalyst-coated surface. The amount of photocatalytic exposure may be controlled by increasing or decreasing the number of perforations 160 and by increasing or decreasing the number of UV light sources 110.

UV light sources 110 may be positioned to emit ultraviolet light into the chamber 115. The wavelength range of ultraviolet light emitted by the UV light source 110 may be approximately between 200 nm to 435 nm, and depending on the type of photocatalyst 170 used, may be around 385 nm to 410 nm. In an exemplary embodiment, the UV light source 110 may be positioned to provide focused ultraviolet light onto the photocatalyst 170. The support(s) 120 may be supported by the chamber 115 proximate to the UV light source 110 so that the surface 125 holding the photocatalyst 170 is in a plane orthogonal to the UV light source 110. The distance of the photocatalyst 170 from the UV light source 110 may be set so that the beam of ultraviolet light (not shown) remains substantially uniform in coverage and intensity. The UV light source 110 may be approximately 1 inch from the photocatalyst 170 on the outermost plates 120a and 120d. It may be appreciated that the use of a UV-LED at such a close distance may provide about 4000 mW/cm$^2$ of intensity. Thus, effective catalysis of air contaminants may be achieved within the air cleaning system 100.

In an exemplary embodiment, the UV light source 110 may be one or more UV LEDs. For example, an array 150 of UV LEDs may be employed. In one exemplary embodiment, the UV light source 110 may include an array 150a on one side 135 of the chamber 115 and an array 150b on an opposite side 145 of the chamber 115. The arrays 150a and 150b may be positioned to emit ultraviolet light orthogonal to airflow, onto the support plate(s) 120 between the two arrays (150a; 150b). For example, the array 150a may be proximate the outermost support plate 120a while the array 150b may be proximate the outermost support plate 120d. The UV light sources 110 may be arranged so that light emitted from adjacent sources may overlap or may irradiate the plates 120 at an angle, thus exposure of the inner plates 120b and 120c through the perforations 160 may be achieved.

Figure 3B:
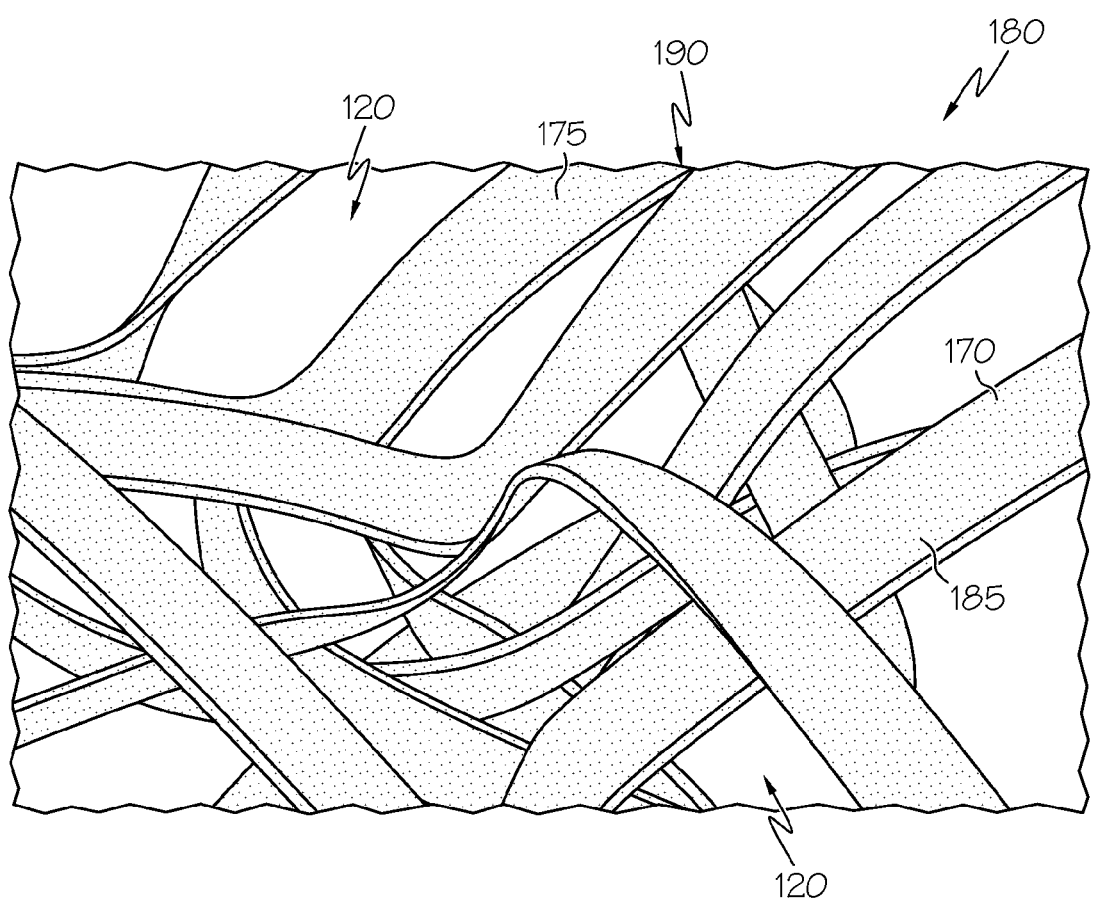
FIG. 3B is a partial enlarged view of the circle 3B in FIG. 3A.

Referring now to FIG. 3B, an enlarged view of circle 3B from FIG. 3A of a section of the plate 120 is shown. In one exemplary embodiment, the reactor 180 may include a plurality of metallic strips 185 on the plate 120. The strips 185 may include a coating 175 of the photocatalyst 170. The metallic strips 185 may be, for example, aluminum. The photocatalyst 170 may be titanium based, for example, titanium dioxide. In an exemplary embodiment, the reactor 180 may be a mesh 190 of the strips 185 attached to the surface 125 configured to allow airflow to pass over and through strips 185. The mesh 190 may provide higher surface area allowing for increased contact of airflow to the coating 175. It may be appreciated that it is advantageous that the Reynolds number for airflow through the reactor 180, and in particular, in contact with the photocatalyst 170 be high enough that flow is nonlaminar.

Figure 4:
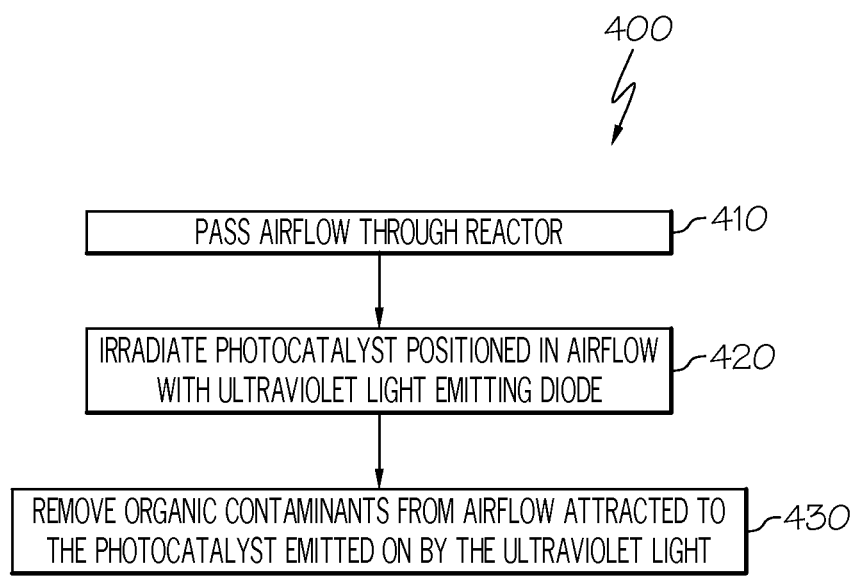
FIG. 4 is an exemplary series of steps in a method of removing organic contaminants from airflow in accordance with another exemplary embodiment of the present invention.

Referring now to FIG. 4, a method 400 is shown in accordance with an exemplary embodiment of the present invention. In step 410, airflow may be passed through a reactor. An ultraviolet light reactive photocatalyst may be attached to the support. In step 420, ultraviolet light may be emitted from an ultraviolet light emitting diode into the airflow and focused onto the photocatalyst. The ultraviolet light may irradiate the photocatalyst orthogonal to the direction of airflow. In step 430, organic contaminants may be removed from airflow that makes contact with the photocatalyst while the ultraviolet light is emitted on the photocatalyst.

It should be understood, of course, that the foregoing relates to exemplary embodiments of the invention and that modifications may be made without departing from the spirit and scope of the invention as set forth in the following claims.

We claim:

1. An air cleaning system, comprising:
   a first array of ultraviolet light emitting diodes (UV-LEDs) disposed in a first plane;
   a second array of UV-LEDs disposed in a second plane that is parallel to the first plane;
   a plurality of planar supports disposed parallel to the first and second planes whereby at least a portion of each of the supports are positioned intermediate the first array and the second array of UV-LEDs;
   wherein the supports each have respective perforations therein;
   wherein all of the respective perforations are defined by respective centerlines;
   wherein all of the respective centerlines, of all of the perforations in any two immediately adjacently disposed supports, are misaligned with one another; and
   a photocatalyst on at least one of the supports and disposed to contact airflow passing across and through the at least one of the supports.

2. The air cleaning system of claim 1, further comprising a chamber, wherein the supports are supported by the chamber so that surfaces of the supports holding the photocatalyst are in a plane orthogonal to the emitted light.

3. The air cleaning system of claim 2, wherein the chamber includes an entrance for the airflow configured to pass the airflow across the surfaces of the supports in a direction orthogonal to the emitted ultraviolet light.

4. The air cleaning system of claim 1 wherein the first array and second array of UV-LEDs emit a wavelength around 385nm to 410 nm.

5. The air cleaning system of claim 4 wherein the photocatalyst is titanium dioxide based.

6. An air cleaning system, comprising:
   a chamber;
   a plurality of support plates in the chamber and spaced parallel to one another, each of the plurality of support plates including a first surface and a second surface opposite the first surface;
   a plurality of strips on at least one of the support plates, wherein each of said strips has at least one flat surface;
   a first plurality of ultraviolet light emitting diodes (UV-LEDs) positioned opposite at least one first surface of the plurality of support plates, and wherein the first plurality of UV-LEDs are positioned over a first cross-sectional area;
   wherein a distance from the first plurality of UV-LEDs to the at least one first surface is such that beams from the first plurality of UV-LEDs are substantially uniform in coverage and intensity on the at least one first surface;
   a second plurality of UV-LEDs positioned opposite at least one second surface of the plurality of support plates, and wherein the second plurality of UV-LEDs are positioned over a second cross-sectional area;
   wherein a distance from the second plurality of UV-LEDs to the at least one second surface is such that beams from the second plurality of UV-LEDs are substantially uniform in coverage and intensity on the at least one second surface;
   wherein the at least one first surface and the at least one second surface define apertures therein;
   wherein the first and second plurality of UV-LEDs are positioned at opposing sides of the chamber; and
   a photocatalyst on the flat strips;
   wherein the at least one first surface and the at least one second surface is disposed to contact an airflow passing across and through the at least one first surface and one second surface;
   wherein the at least one first surface and the at least one second surface have respective cross sectional areas that respectively overlap all of the first and second cross-sectional areas of the first and second pluralities of UV-LEDs.

7. The air cleaning system of claim 6 wherein the first and second plurality of UV-LEDs are arranged as arrays.

8. The air cleaning system of claim 7 wherein the first plurality of UV-LEDs includes a first set of UV-LEDs positioned proximate a first outermost support plate and the second plurality of UV-LEDs includes a second set of UV-LEDs positioned proximate a second outermost support plate, the second outermost support plate positioned on an opposing side of the chamber from the first outermost support plate, wherein the first set of UV-LEDs is positioned on an outward facing side of the first outermost support plate and the second set of UV-LEDs is positioned an outward side of the second outermost support plate.

9. The air cleaning system of claim 8 wherein the first and second sets of UV-LEDs are configured to emit the ultraviolet light focused onto the first and second outermost support plates.

10. The air cleaning system of claim 6 wherein the chamber includes an entrance for the airflow configured to pass the airflow across the plurality of support plates in a direction orthogonal to the emitted ultraviolet light.

11. The air cleaning system of claim 6 wherein the photocatalyst is titanium dioxide based.

* * * * *